(12) United States Patent
Boyd et al.

(10) Patent No.: US 8,771,239 B2
(45) Date of Patent: *Jul. 8, 2014

(54) DRIVE MECHANISMS SUITABLE FOR USE IN DRUG DELIVERY DEVICES

(75) Inventors: Malcolm Boyd, Warwickshire (GB); Richard Letham, Surrey (GB); David Plumptre, Worcestershire (GB); Robert Veasey, Warwickshire (GB); James May, Kenilworth (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/173,445

(22) Filed: Jun. 30, 2011

(65) Prior Publication Data

US 2012/0172816 A1 Jul. 5, 2012

Related U.S. Application Data

(63) Continuation of application No. 12/466,596, filed on May 15, 2009, now Pat. No. 7,993,301, which is a continuation of application No. PCT/EP2007/009676, filed on Nov. 8, 2007.

(30) Foreign Application Priority Data

Nov. 17, 2006 (EP) .................... 06023951

(51) Int. Cl.
 *A61M 5/30* (2006.01)
 *A61M 5/00* (2006.01)
(52) U.S. Cl.
 USPC .......................................... 604/208; 604/211
(58) Field of Classification Search
 USPC ............. 604/68–72, 131, 181, 187, 207–211, 604/224, 228
 See application file for complete search history.

(56) References Cited

U.S. PATENT DOCUMENTS

| 5,782,633 A | 7/1998 | Mühlbauer | |
|---|---|---|---|
| 7,993,301 B2 * | 8/2011 | Boyd et al. | 604/68 |
| 2004/0064104 A1 * | 4/2004 | Miller et al. | 604/207 |

FOREIGN PATENT DOCUMENTS

| WO | 96/26754 A2 | 9/1996 |
| WO | 01/95959 A1 | 12/2001 |
| WO | 03/080160 A1 | 10/2003 |

* cited by examiner

*Primary Examiner* — Matthew F Desanto
(74) *Attorney, Agent, or Firm* — McDonnell Boehnen Hulbert & Berghoff LLP

(57) ABSTRACT

The present invention relates to drive mechanisms suitable for use in drug delivery devices, in particular pen-type injectors, wherein a number of pre-set doses of medicinal product can be administered. In particular, the present invention relates to such drug delivery devices where a user may activate the drug delivery device.

11 Claims, 13 Drawing Sheets

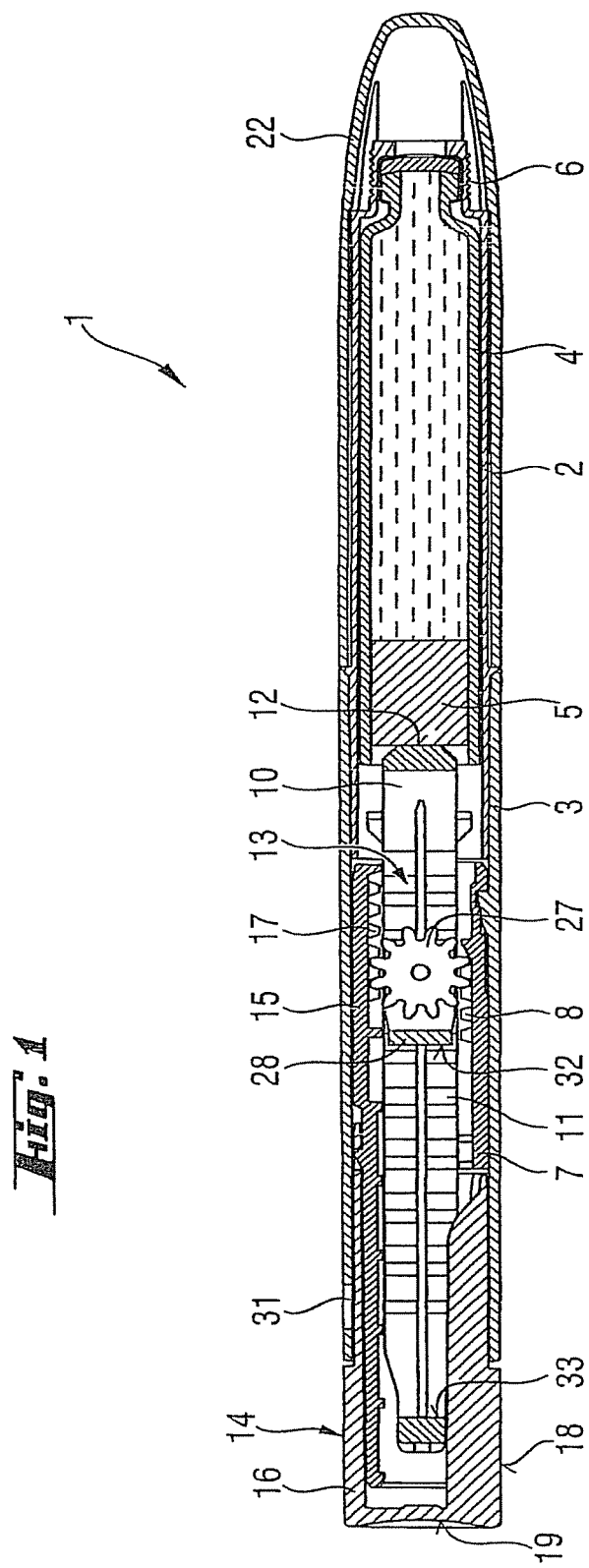

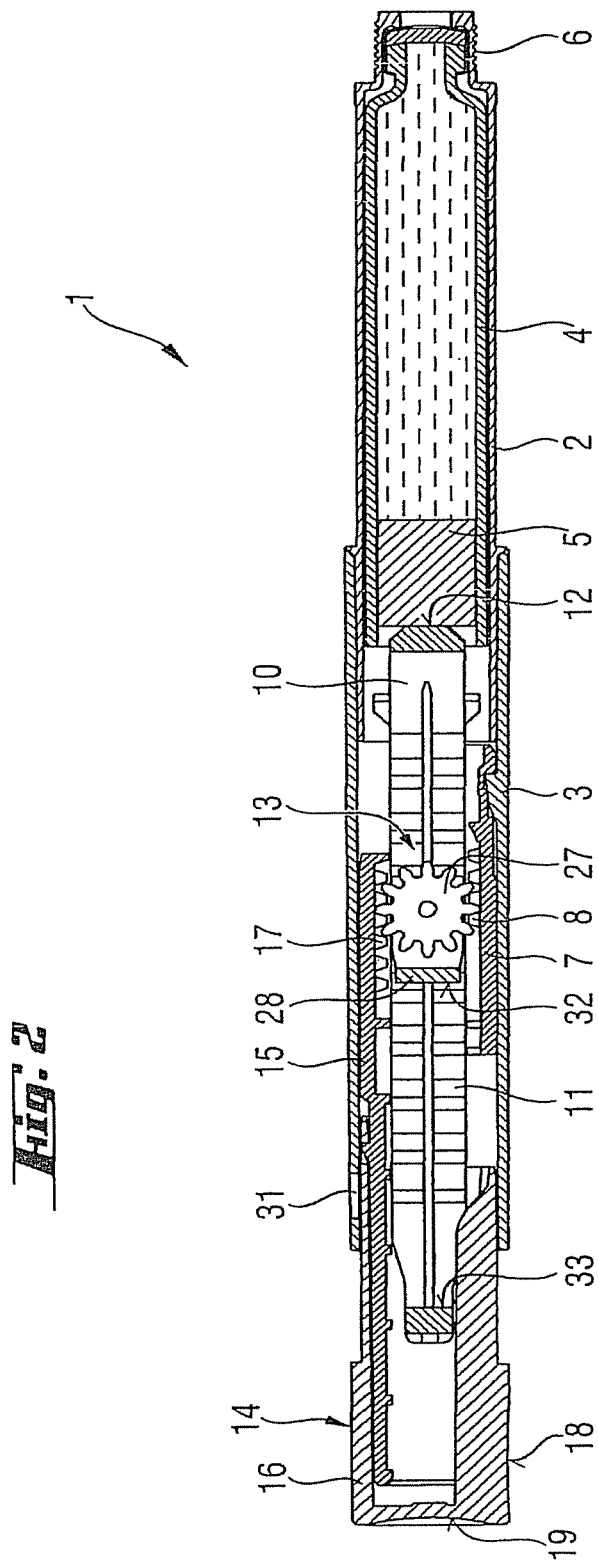

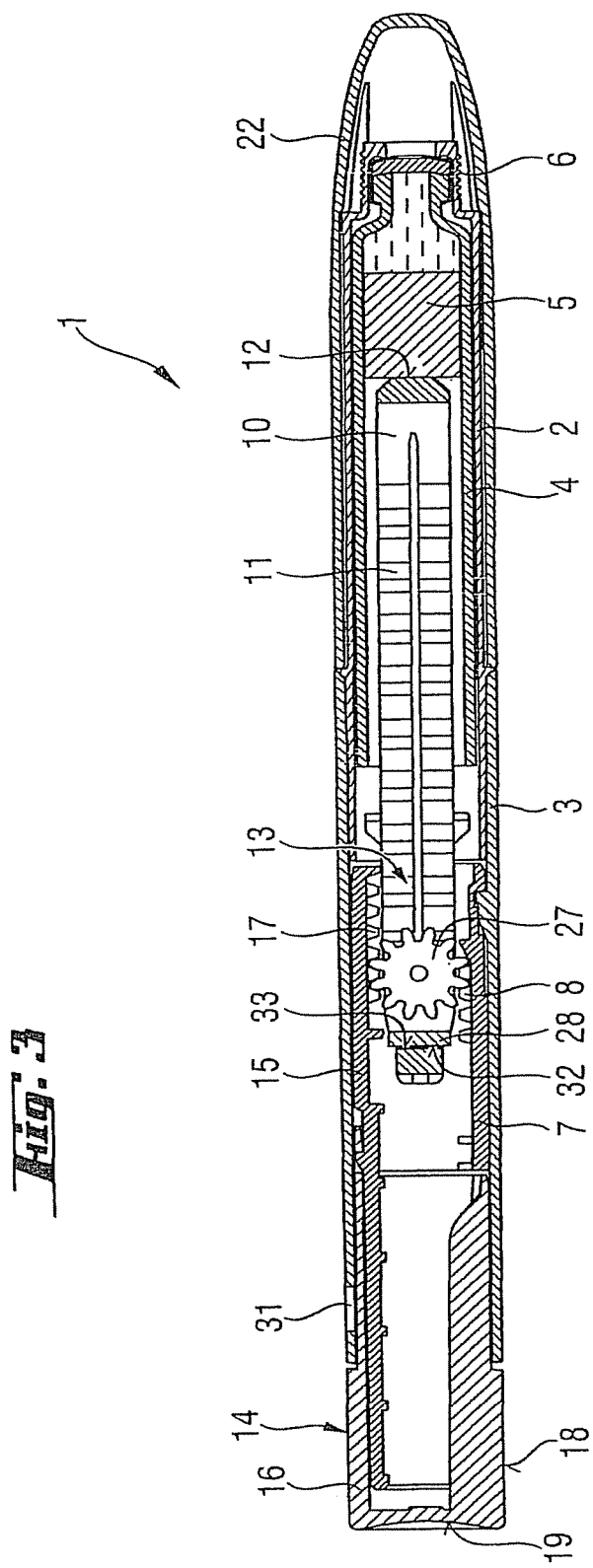

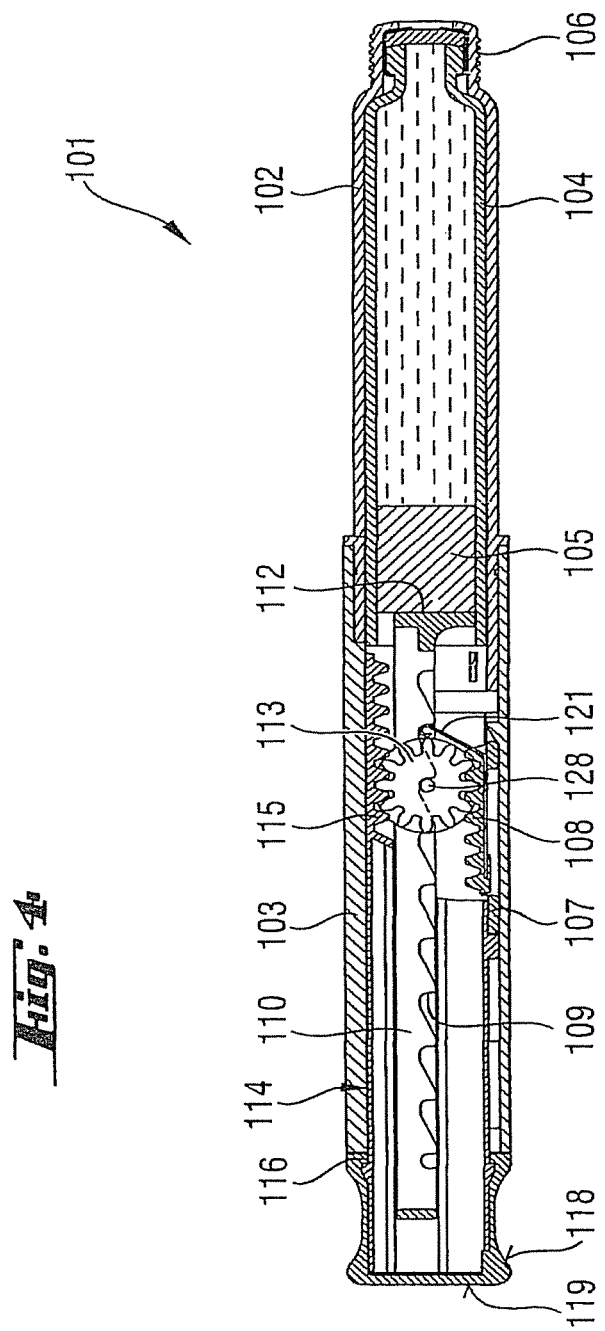

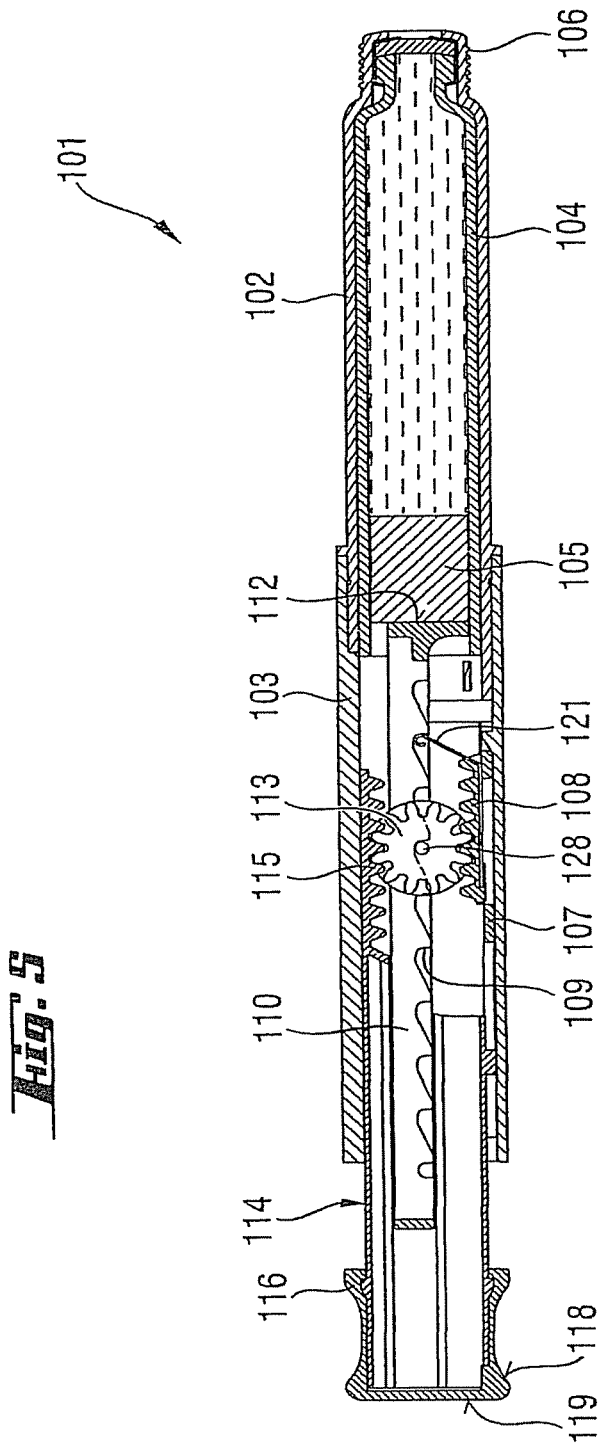

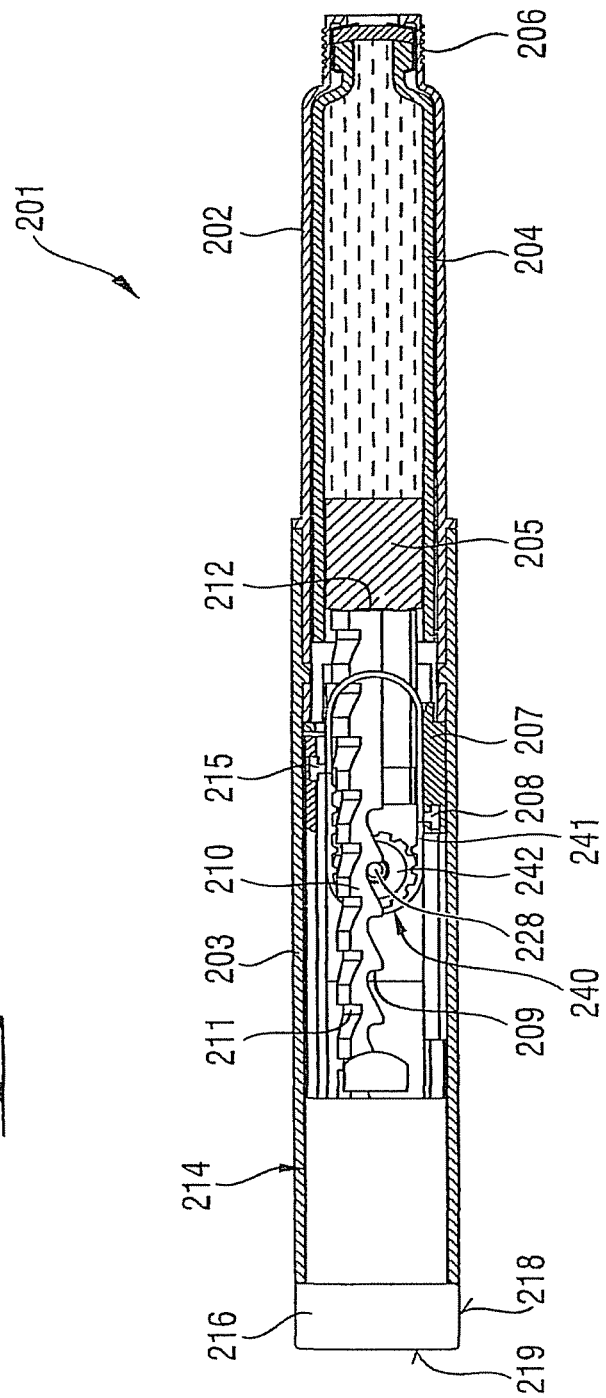

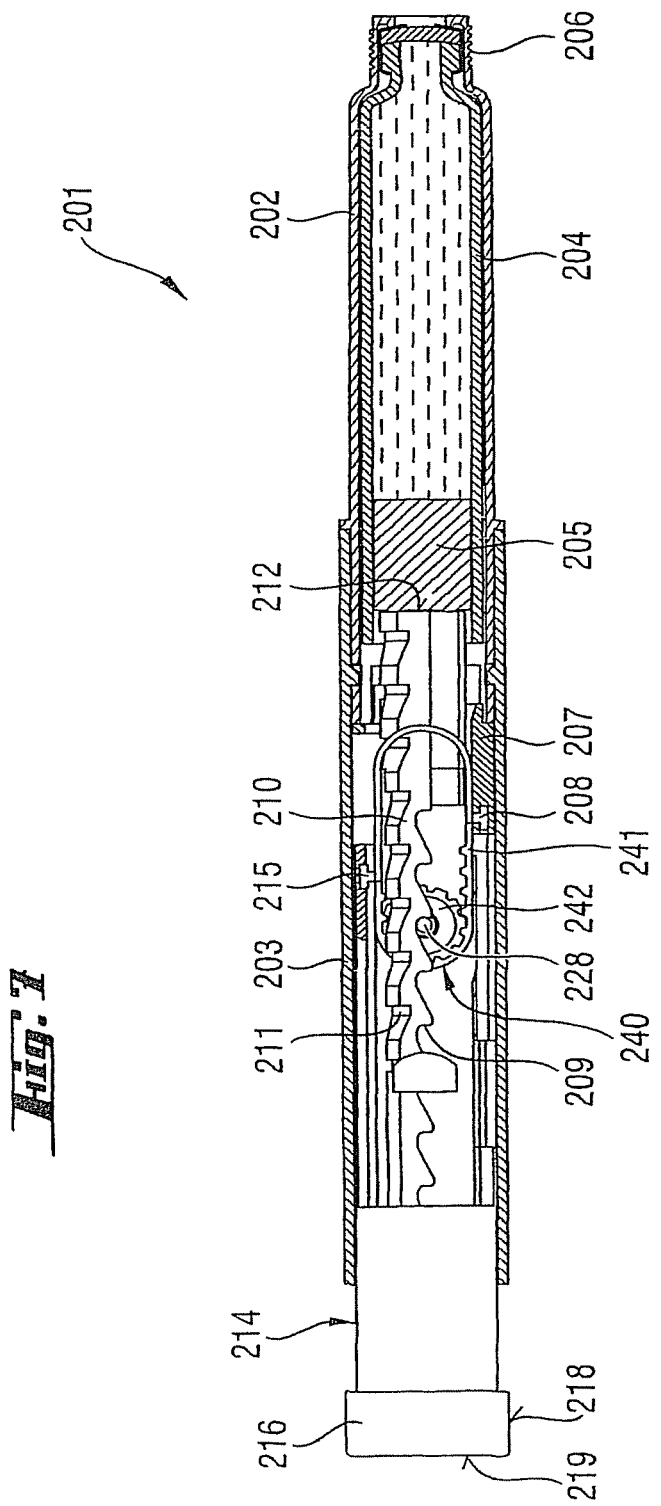

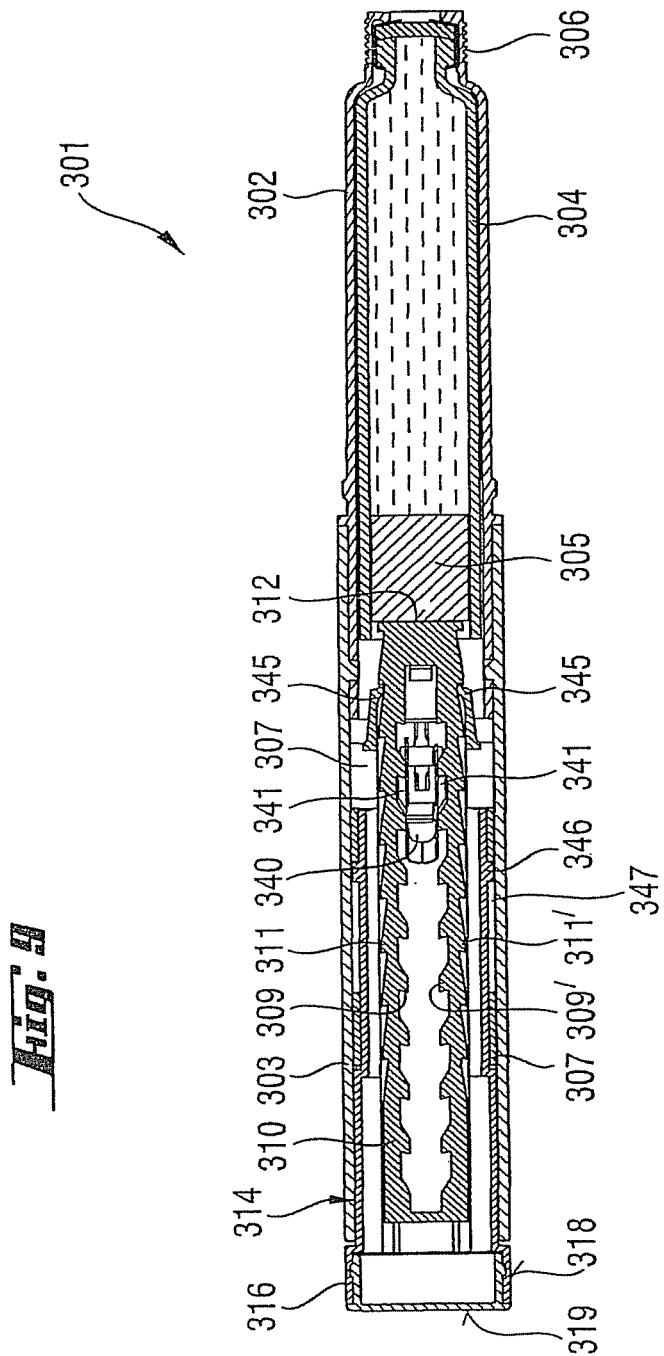

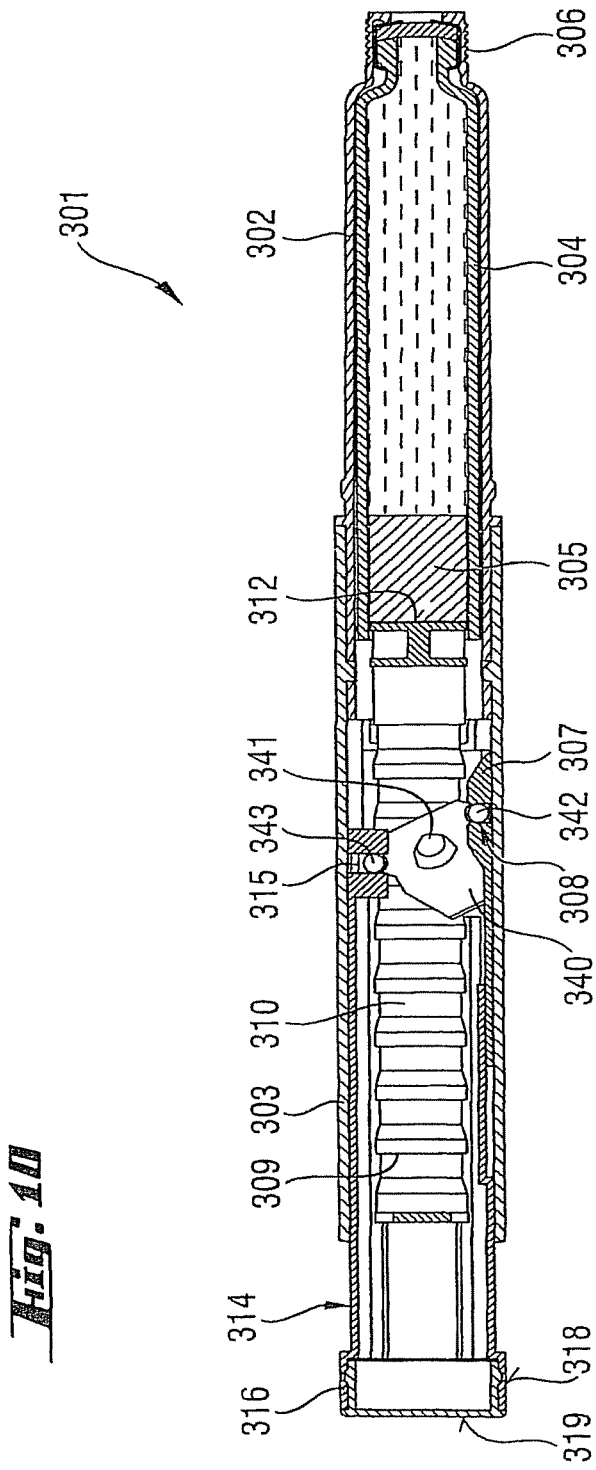

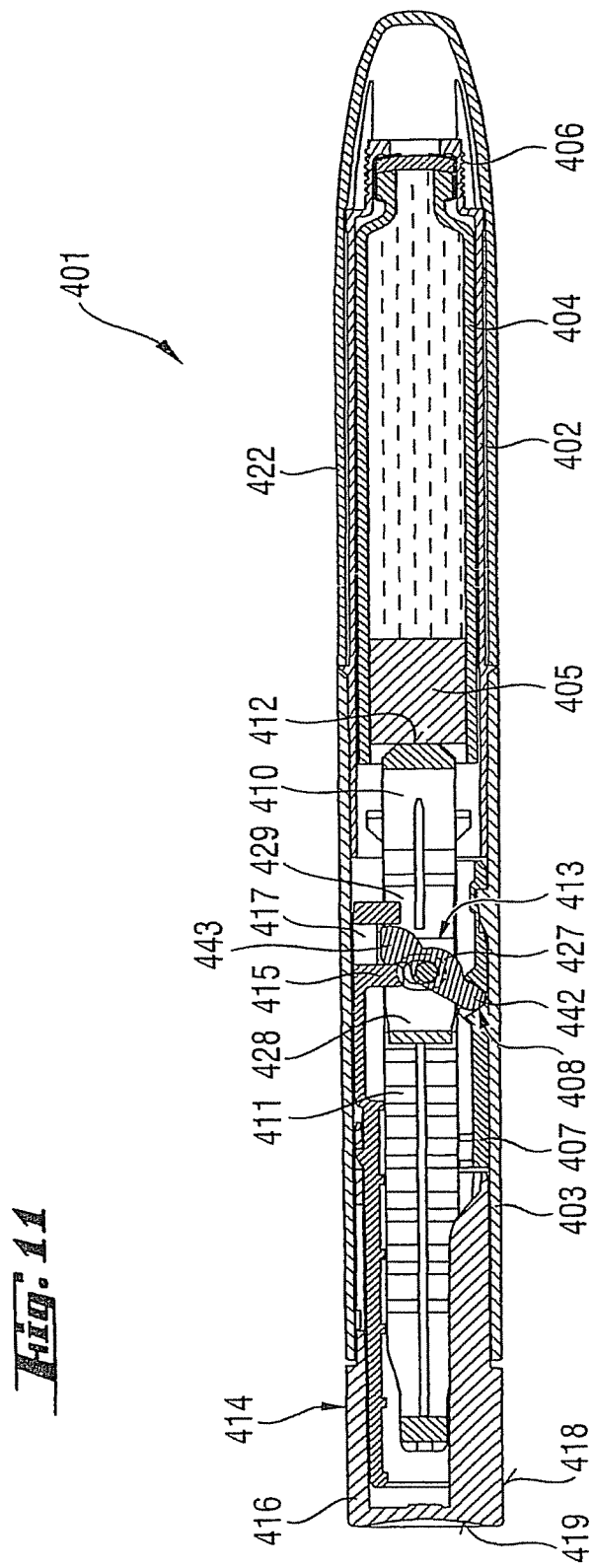

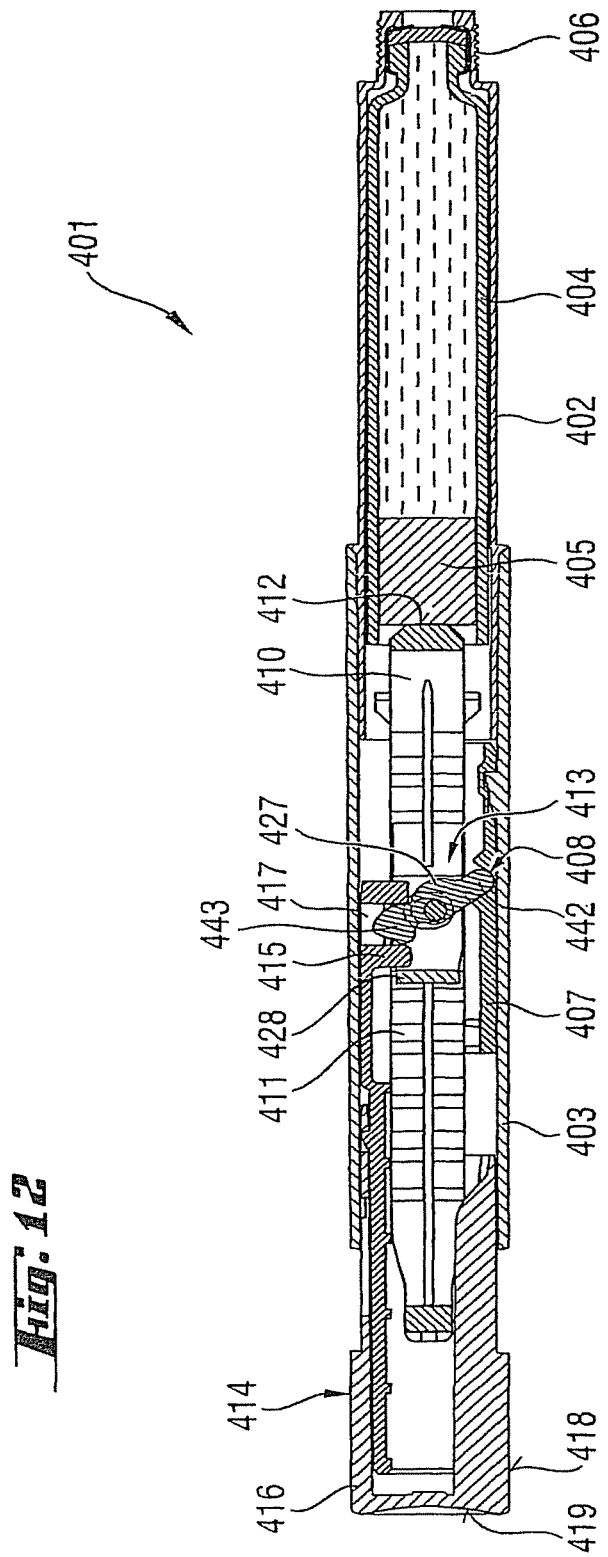

DRIVE MECHANISMS SUITABLE FOR USE IN DRUG DELIVERY DEVICES

CROSS REFERENCE TO RELATED APPLICATIONS

The present application is a continuation application of Ser. No. 12/466,596 filed May 15, 2009 now U.S. Pat. No. 7,993,301 which is a continuation of PCT/EP2007/009676 filed Nov. 8, 2007 and claims priority to European Patent Application No. 06023951.4, filed Nov. 17, 2006, the entire contents of which are incorporated entirely herein by reference.

THE TECHNICAL FIELD OF THE INVENTION

The present invention relates to drive mechanisms suitable for use in drug delivery devices, in particular pen-type injectors, wherein a number of pre-set doses of medicinal product can be administered. In particular, the present invention relates to such drug delivery devices where a user may activate the drug delivery device.

DESCRIPTION OF THE RELATED ART

Such drug delivery devices have application where persons without formal medical training, i.e., patients, need to administer an accurate and predefined dose of a medicinal product, such as heparin or insulin. In particular, such devices have application where medicinal product is administered on an irregular basis over a short-term or long-term period.

These circumstances set a number of requirements for drug delivery devices of this kind. The device must be robust in construction, yet easy to use in terms of the manipulation of the parts, understanding by a user of its operation and the delivery of the required dose of medicament. Dose setting must be easy and unambiguous. Where the device is to be disposable rather than reusable, the device should be cheap to manufacture and easy to dispose of (preferably being suitable for recycling). To meet these requirements the number of parts required to assemble the device and the number of material types the device is made from need to be kept to a minimum.

User operated drug delivery devices are well known within the medical field.

WO 9626754 A2 teaches a mechanism for accurate dispensing of pre-set quantities of medicament from a syringe wherein a rotatable plunger has a number of parallel racks on its internal surface each of which comes into engagement with a first tooth wheel as the plunger rotates when a dose is set. The device has a second tooth wheel that rotates with the first tooth wheel thus driving a thrust rod into the syringe when the selected dose is delivered. Whilst this device provides a useful embodiment for administering a pre-set dose the intuitiveness of setting a dose remains unsolved as parts need to be rotated during dose setting.

An injection device is disclosed in WO 01/95959 A1 having a gearbox in which a dose is set by rotating a dose setting member and the gearbox, and by which an injection button elevates from an end of the syringe a distance proportional to the set dose and wherein the set dose can be injected by pressing home the injection button to its not elevated position. Whilst this device provides a useful embodiment for administering a pre-set dose once again the intuitiveness of setting a dose remains unsolved as parts need to be rotated during dose setting.

U.S. Pat. No. 5,782,633 teaches an applicator for a dental compound having an elongated implement body and a gear-wheel/pinion pair connected to two moving racks, one rack located on a pusher rod and another rack located on a ram.

In WO 03/080160 A1 a medication dispensing apparatus having a gear set is disclosed wherein the gear set consists of a first pinion in meshed engagement with a rack of a plunger and a second pinion in meshed engagement with a rack of a drive member of the apparatus to provide the apparatus with a mechanical advantage. The first pinion and the second pinion are both independent components having a unidirectional coupling set between.

Surprisingly it was found that the drive mechanism according to instant invention without having two pinions provides a valuable technical alternative for push-pull drive mechanisms, wherein reduced force is needed to actuate the mechanism. This is achieved by the introduction of a piston rod and rotating means as defined by instant invention. Further the drive mechanism according to instant invention further provides the advantage of intuitive and easy to use dose setting.

DESCRIPTION OF THE INVENTION

According to a first aspect of the present invention, a drive mechanism for use in a drug delivery device is provided comprising:
 a housing having a proximal and a distal end;
 a drive member located within the said housing such that the said drive member is movable longitudinally;
 a piston rod adapted to operate through the housing and transfer a force in the longitudinal direction to the distal end of the drug delivery device;
 a rotating means releasably engaged with the said piston rod and engaged to the said drive member and engaged to the said housing;
 characterized in that,
 a) when the said drive member moves proximally with respect to the said housing the said rotating means moves proximally with respect to the said piston rod;
 b) when the said drive member moves distally the said rotating means moves distally displacing the said piston rod towards the distal end of the device.

In a preferred embodiment of the drive mechanism of instant invention the said drive member is non-rotatable with respect to the said housing.

In another preferred embodiment of the drive mechanism of instant invention the said piston rod is non-rotatable with respect to the said housing.

In a further preferred embodiment of the drive mechanism of instant invention the rotating means is a gear.

In yet a further preferred embodiment of the drive mechanism of instant invention the gear is free to translate relative to the said piston rod.

In another further preferred embodiment of the drive mechanism of instant invention the engagement between the piston rod and the gear acts through the axle of the said gear.

In yet another further preferred embodiment of the drive mechanism of instant invention the gear is designed to be engaged with a rack located on the drive member and a rack located on the housing.

In a further embodiment of the drive mechanism of instant invention the rotating means is a lever.

In yet another embodiment of the drive mechanism of instant invention the rotating means is a pulley.

In yet a further embodiment of the drive mechanism of instant invention the rotating means is a lever assembly.

The term "drug delivery device" according to instant invention shall mean a single-dose or multi-dose or pre-set dose or pre-defined, disposable or re-useable device designed to dispense a user selectable or pre-defined dose of a medicinal product, preferably multiple pre-defined doses, e.g. insulin, growth hormones, low molecular weight heparins, and their analogues and/or derivatives etc. Said device may be of any shape, e.g. compact or pen-type. Dose delivery may be provided through a mechanical (optionally manual) or electrical drive mechanism or stored energy drive mechanism, such as a spring, etc. Dose selection may be provided through a manual mechanism or electronic mechanism. Additionally, said device may contain components designed to monitor physiological properties such as blood glucose levels, etc. Furthermore, the said device may comprise a needle or may be needle-free. In particular, the term "drug delivery device" shall mean a disposable needle-based pen-type device providing multiple pre-defined doses having mechanical and manual dose delivery and dose selection mechanisms, which is designed for use by persons without formal medical training such as patients. Preferably, the drug delivery device is of the injector-type.

The term "housing" according to instant invention shall preferably mean any exterior housing ("main housing", "body", "shell") or interior housing ("insert", "inner body") having a unidirectional axial coupling to prevent proximal movement of specific components. The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge from which a number of doses of a medicinal product may by dispensed.

In a more specific embodiment of instant invention, the exterior housing is provided with a plurality of maximum dose stops adapted to be abutted by an axial stop provided on the drive member.

The term "engaged" according to instant invention shall particularly mean the interlocking of two or more components of the drive mechanism/drug delivery device, e.g. a spline, thread, or meshed teeth connection, preferably the interlocking of meshed teeth of components.

The term "drive member" according to instant invention shall mean any component adapted to operate through/within the housing, designed to translate axial movement through/within the drug delivery device, preferably from an actuation means to the piston rod. In a preferred embodiment the drive member is further releasably engaged with the piston rod. The drive member may be of unitary or multipart construction.

The term "releasably engaged" according to instant invention shall preferably mean that two components of instant mechanism or device are joined for translation of force or movement in one direction only, preferably during dispense.

The term "piston rod" according to instant invention shall mean a component adapted to operate through/within the housing, designed to translate axial movement through/within the drug delivery device, preferably from the drive member to the piston, for the purpose of discharging/dispensing an injectable product. Said piston rod may be flexible or not. It may be a simple rod, a lead-screw, a rack and pinion system, a worm gear system, or the like. The "piston rod" shall further mean a component having a circular or non-circular cross-section. It may be made of any suitable material known by a person skilled in the art and may be of unitary or multipart construction. In a preferred embodiment, the piston rod comprises a series of one or more sets of longitudinally spaced ribs and/or indentations.

The term "rotating means" according to instant invention shall mean any rotating component that transfers force and/or movement from the drive member to the piston rod. It may be made of any suitable material known by a person skilled in the art and may be of unitary or multipart construction. In a preferred embodiment the rotating means may be a gear component, more preferably a spur gear. In another preferred embodiment the rotating means may be a lever. In yet another preferred embodiment the rotating means may be a pulley. In yet a further preferred embodiment the rotating means may be a lever assembly.

The term "gear" according to instant invention shall mean a toothed wheel used in conjunction with a rack and/or another gear, preferably a rack, to transmit force and/or motion. In a preferred embodiment the gear may be a spur gear. In yet another preferred embodiment the term "gear" means a gear wheel mounted within a carrier.

The term "lever" according to instant invention shall mean any beam component pivoted about a fulcrum to transmit force and/or motion. In a preferred embodiment the fulcrum point is located on the housing and load is applied through the drive member. In yet another preferred embodiment the term "lever" shall mean any beam component that moves essentially proximally with respect to the piston rod during dose setting and that moves essentially distally with respect to the piston rod during dose delivery.

The term "pulley" according to instant invention shall mean any wheel and/or belt component that is designed to transmit force and/or motion. In a preferred embodiment the pulley comprises a wheel and belt. In a more preferred embodiment the belt of the pulley is attached to the housing and the drive member and the wheel of the pulley engages with the piston rod and the belt of the pulley. In yet another preferred embodiment the wheel of the pulley is releasably engaged with the piston rod.

The term "lever assembly" according to instant invention shall mean any component consisting of a lever and a carrier designed to transmit force and/or motion.

The term "rack" according to instant invention shall mean any component having a linear array of ribs and/or indentations and/or gear-form teeth. In a preferred embodiment a rack is located in the housing and a further rack is located in the drive member. In a further preferred embodiment one and/or both, more preferably one, of the racks located on the housing or on the drive member is flexible and/or pivoted and/or movable in one or more axis, more preferably one.

The term "graphical status indicator" according to instant invention shall preferably mean any markings, symbols, numerals, etc., e.g. printed on the external surface of a component of the device, for example the drive sleeve or an odometer or a dose dial sleeve, or the like, preferably the drive sleeve, for indicating to the user when the device has been activated and/or is in operation and/or direction of operation and/or a dose of medicament has been delivered.

The "distal end" of the device or a component of the device shall mean the end, which is closest to the dispensing end of the device.

The "proximal end" of the device or a component of the device shall mean the end, which is furthest away from the dispensing end of the device.

A second aspect of instant invention provides an assembly for use in a drug delivery device comprising the drive mechanism according to instant invention.

A third aspect of the present invention provides a drug delivery device comprising the drive mechanism or the assembly according to instant invention.

A fourth aspect of the present invention provides a method of assembling a drug delivery device comprising the step of providing a drive mechanism or an assembly according to instant invention.

A fifth aspect of instant invention is the use of a drug delivery device according to instant invention for dispensing a medicinal product preferably dispensing a pharmaceutical formulation (e.g. solution, suspension etc.) comprising an active compound selected from the group consisting of insulin, growth hormone, low molecular weight heparin, their analogues and their derivatives.

BRIEF DESCRIPTION OF THE DRAWINGS

Without any limitation, the instant invention will be explained in greater detail below in connection with a preferred embodiment and with reference to the drawings in which:

FIG. 1 shows a sectional view of a first embodiment of the drug delivery device in accordance with the present invention in a first, cartridge full, position;

FIG. 2 shows a sectional view of a first embodiment of the drug delivery device in accordance with the present invention in a second, first dose set, position;

FIG. 3 shows a sectional view of a first embodiment of the drug delivery device in accordance with the present invention in a third, final dose dispensed, position;

FIG. 4 shows a sectional view of a second embodiment of the drug delivery device in accordance with the present invention in a first, cartridge full, position;

FIG. 5 shows a sectional view of a second embodiment of the drug delivery device in accordance with the present invention in a second, first dose set, position;

FIG. 6 shows a sectional view of a third embodiment of the drug delivery device in accordance with the present invention in a first, cartridge full, position;

FIG. 7 shows a sectional view of a third embodiment of the drug delivery device in accordance with the present invention in a second, first dose set, position;

FIG. 9 shows a further sectional view of a fourth embodiment of the drug delivery device in accordance with the present invention in a first, cartridge full, position;

FIG. 10 shows a sectional view of a fourth embodiment of the drug delivery device in accordance with the present invention in a second, first dose set, position.

FIG. 11 shows a sectional view of a fifth embodiment of the drug delivery device in accordance with the present invention in a first, cartridge full, position;

FIG. 12 shows a sectional view of a fifth embodiment of the drug delivery device in accordance with the present invention in a second, first dose set, position.

DETAILED DESCRIPTION OF THE EMBODIMENTS

Example 1

Figure 1A:
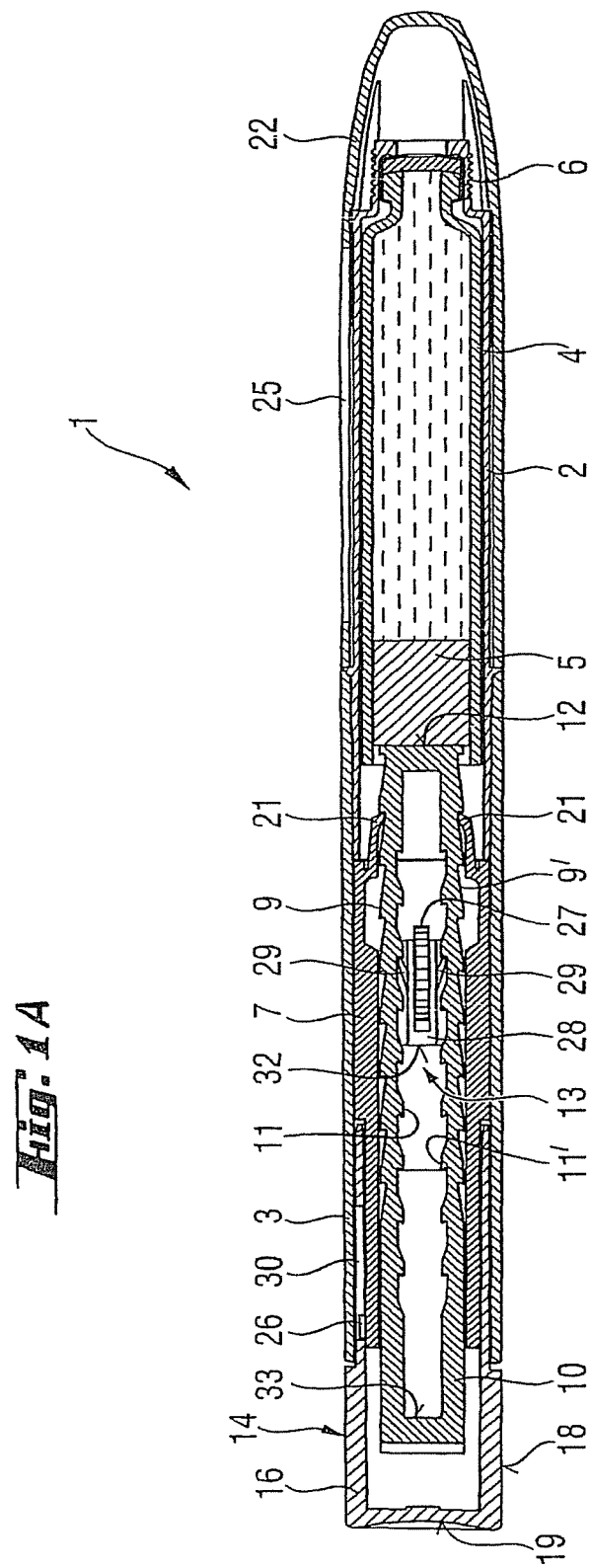
FIG. 1A shows a further sectional view of a first embodiment of the drug delivery device in accordance with the present invention in a first, cartridge full, position.

Referring first to FIGS. 1 to 3, there is shown a drug delivery device in accordance with the present invention.

The drug delivery device (1) comprises a cartridge retaining part (2), and a main (exterior) housing part (3). The proximal end of the cartridge retaining part (2) and the distal end of the main housing (3) are secured together by any suitable means known to the person skilled in the art. In the illustrated embodiment, the cartridge retaining part (2) is secured within the distal end of the main housing part (3).

A cartridge (4) from which a number of doses of a medicinal product may be dispensed is provided in the cartridge retaining part (2). A piston (5) is retained in the proximal end of the cartridge (4).

A removable cap (22) is releasably retained over the distal end of the cartridge retaining part (2). The removable cap (22) may be optionally provided with one or more window apertures through which the position of the piston (5) within the cartridge (4) can be viewed.

The distal end of the cartridge retaining part (2) in the illustrated embodiment, is provided with a distal threaded region (6) designed for the attachment of a suitable needle assembly to enable medicament to be dispensed from the cartridge (4).

In the illustrated embodiment, the main housing part (3) is provided with an internal housing (7). The internal housing (7) is secured against rotational and/or axial movement with respect to the main housing part (3). The internal housing (7) is provided with a rack (8) extending along the main axis of the internal housing (7). Alternatively, the internal housing (7) may be formed integrally with the main housing part (3). Additionally, the internal housing (7) is provided with a plurality of guide lugs (not shown) and pawl means (not shown). The pawl means may be an integrated part of the internal housing (7) or may be a separate component as illustrated.

A piston rod (10) extending through the main housing (3) has a first set of indentations (not shown) extending longitudinally along external surfaces of the piston rod (10). A second set of indentations (11) extend longitudinally along internal surfaces of the piston rod (10). The first set of indentations of the piston rod (10) extend through and are engaged with the pawl means of the internal housing (7) to prevent movement of the piston rod (10) in the proximal direction during setting of the device. A bearing surface (12) located at the distal end of the piston rod (10) is disposed to abut the proximal face of the piston (5). In the illustrated embodiment the longitudinal spacing of the first set of indentations and the second set of indentations (11) is essentially equal.

A gear (13), consisting of a carrier (28) and a gear wheel (27), free to rotate within the carrier (28), is located within a channel within the piston rod (10). Pawl arms (29) located on the carrier (28) are releasably engaged with the second set of indentations (11) of the piston rod (10). The pawl arms (29) of the carrier (28) are designed to transmit force to the piston rod (10) in the distal direction during dispense and to allow relative movement between the gear (13) and the piston rod (10) in the proximal direction during setting. The teeth of the gear wheel (27) are permanently engaged with the teeth of the rack (8) of the internal housing (7).

A drive member (14) extends about the piston rod (10). The drive member (14) comprises a rack part (15) and an activation part (16). The rack part (15) and the activation part (16) are secured to each other to prevent rotational and/or axial movement there between. Alternatively, the drive member (14) may be a unitary component consisting of an integrated rack part (15) and activation part (16).

The rack part (15) is provided with a rack (17) extending along the main axis of the rack part (15). The teeth of the rack (17) of the rack part (15) are permanently engaged with the teeth of the gear wheel (27).

The drive member (14) has a plurality of guide slots (not shown) in which the guide lugs (not shown) of the internal housing (7) are located. These guide slots define the extent of permissible axial movement of the drive member (14) with respect to the housing part (3). In the illustrated embodiment the guide slots also prevent rotational movement of the drive member (14) relative to the main housing part (3).

The activation part (16) of the drive member (14) has a plurality of grip surfaces (18) and a dispensing face (19).

To increase intuitiveness of the operation of the device, the main housing part (3) may optionally be provided with a window aperture through which graphical status indicators provided on the drive member (14), can be viewed.

Operation of the drug delivery device in accordance with the present invention will now be described.

To set a dose a user grips the grip surfaces (18) of the drive member (14). The user then pulls the drive member (14) in a proximal direction away from the main housing part (3) thereby moving the rack part (15) in a proximal direction.

The proximal movement of the rack part (15) causes the gear wheel (27) to rotate and move proximally by virtue of the engagement of the teeth of the gear wheel (27) of the gear (13) with the teeth of the rack (17) of the rack part (15) and the teeth of the rack (8) of the internal housing (7) thus moving the gear (13) in the proximal direction.

The piston rod (10) is prevented from moving proximally by interaction of pawl means of the internal housing (7) with a first set of indentations on the piston rod (10). As the drive member (14) travels in the proximal direction relative to the piston rod (10), the pawl arms (29) of the carrier (28) are displaced inwardly by interaction with the second set of indentations (11) of the piston rod (10).

The proximal travel of the drive member (14) is limited by the guide slots of the rack part (15). At the end of the travel of the drive member (14), the pawl arms (29) of the carrier (28) engage with the next sequential indentation of the second set of indentations (11) of the piston rod (10) as indicated in FIG. 2. The action of the pawl arms (29) of the carrier (28) positively engaging the second set of indentations (11) of the piston rod (10) creates an audible and tactile feedback to the user to indicate that the dose has been set. Additionally, visual feedback regarding dose setting may optionally be indicated by a graphical status indicator provided on the drive member (14), which can be viewed through an optional window aperture in the main housing part (3).

When the dose has been set, the user may then dispense this dose by depressing the dispensing face (19) of the activation part (16) of the drive member (14). By this action the drive member (14) and the rack part (15) are moved axially in the distal direction relative to the main housing part (3). As the teeth of the gear wheel (27) of the gear (13) are engaged with the teeth of the rack (17) of the rack part (15) and the teeth of the rack (8) of the internal housing (7), the gear wheel (27) of the gear (13) is caused to rotate and move in the distal direction thus moving the gear (13) longitudinally in the distal direction. As the pawl arms (29) of the carrier (28) of the gear (13) are engaged with the second set of indentations (11) of the piston rod (10), the piston rod (10) is caused to move longitudinally in the distal direction with respect to the internal housing (7).

The distal axial movement of the piston rod (10) causes the bearing surface (12) of the piston rod (10) to bear against the piston (5) of the cartridge (4) causing a dose of medicament to be dispensed through the attached needle (not shown).

The distal travel of the drive member (14) is limited by the guide slots (not shown) of the rack part (15). Audible and tactile feedback to indicate that the dose has been dispensed is provided by the interaction of the pawl means (not shown) of the internal housing (7) with the first set of indentations (not shown) of the piston rod (10). Additionally, visual feedback regarding dose dispensing may optionally be indicated by a graphical status indicator, provided on the drive member (14), which can be viewed through an optional window aperture in the main housing part (3).

Further doses may be delivered as required up to a predetermined maximum number of doses. FIG. 3 shows the drug delivery device of instant invention in a condition where the maximum number of doses has been delivered. In this condition the proximal face (32) of the carrier (28) abuts an internal distal face (33) of the piston rod (10) to prevent further axial movement of the gear (13) and thus the drive member (14) in proximal direction.

Example 2

Referring to FIGS. 4 to 5, there is shown an alternative embodiment of the drug delivery device in accordance with the present invention.

The drug delivery device (101) comprises a cartridge retaining part (102), and a main (exterior) housing part (103). The proximal end of the cartridge retaining part (102) and the distal end of the main housing (103) are secured together by any suitable means known to the person skilled in the art. In the illustrated embodiment, the cartridge retaining part (102) is secured within the distal end of the main housing part (103).

A cartridge (104) from which a number of doses of a medicinal product may be dispensed is provided in the cartridge retaining part (102). A piston (105) is retained in the proximal end of the cartridge (104).

The distal end of the cartridge retaining part (102) in the illustrated embodiment, is provided with a distal threaded region (106) designed for the attachment of a suitable needle assembly (not shown) to enable medicament to be dispensed from the cartridge (104).

In the illustrated embodiment, the main housing part (103) is provided with an internal housing (107). The internal housing (107) is secured against rotational and/or axial movement with respect to the main housing part (103). The internal housing (107) is provided with a flexible rack (108) extending along the main axis of the internal housing (107). Alternatively, the internal housing (107) may be formed integrally with the main housing part (103). Additionally, the internal housing (107) is provided with a plurality of guide slots (not shown) and pawl means (121).

A piston rod (110) extending through the main housing (103) has a set of teeth (109) extending longitudinally along a surface of the piston rod (110). The set of teeth (109) of the piston rod (110) extend through and are engaged with the pawl means (121) of the internal housing (107) to prevent movement of the piston rod (110) in the proximal direction during setting of the device. A bearing surface (112) located at the distal end of the piston rod (110) is disposed to abut the proximal face of the piston (105).

A gear (113) is located within a channel within the piston rod (110). An axle (128) of the gear (113) is releasably engaged with the set of teeth (109) of the piston rod (110). The set of teeth (109) are designed to allow force transmission to the piston rod (110) in the distal direction during dispense and to allow relative movement between the gear (113) and the piston rod (110) in the proximal direction during setting. The teeth of the gear (113) are permanently engaged with the teeth of the flexible rack (108) of the internal housing (107).

A drive member (114) extends about the piston rod (110). The drive member (114) comprises a rack (115) and an activation part (116). The rack (115) and the activation part (116) are secured to each other to prevent rotational and/or axial movement there between. Alternatively, the drive member (114) may be a unitary component consisting of an integrated rack (115) and activation part (116).

The teeth of the rack (115) are permanently engaged with the teeth of the gear (113).

The drive member (114) has a plurality of guide lugs (not shown) which are located in the guide slots (not shown) of the internal housing (107). This defines the extent of permissible axial movement of the drive member (114) with respect to the housing part (103). In the illustrated embodiment the guide slots also prevent rotational movement of the drive member (114) relative to the main housing part (103).

The activation part (116) of the drive member (114) has a grip surface (118) and a dispensing face (119).

To increase intuitiveness of the operation of the device, the main housing part (103) may optionally be provided with a window aperture through which optional graphical status indicators, provided on the drive member (114), can be viewed.

Operation of the drug delivery device in accordance with the present invention will now be described.

To set a dose a user grips the grip surfaces (118) of the drive member (114). The user then pulls the drive member (114) in a proximal direction away from the main housing part (103) thereby moving the rack (115) in a proximal direction.

The proximal movement of the rack (115) causes the gear (113) to rotate and move proximally by virtue of the engagement of the teeth of the gear (113) with the teeth of rack (115) and the teeth of the flexible rack (108) of the internal housing (107).

The piston rod (110) is prevented from moving proximally by interaction of pawl means (121) of the internal housing (107) with set of teeth (109) of the piston rod (110). As the drive member (114) travels in the proximal direction relative to the piston rod (110), the axle (128) of the gear (113) is displaced transversely by interaction with the set of teeth (109) of the piston rod (110) thus deflecting the flexible rack (108) of the internal housing (107).

The proximal travel of the drive member (114) is limited by the guide slots (not shown) of the internal housing (107). At the end of the travel of the drive member (114), the axle (128) of the gear (113) engages with the next sequential tooth of the set of teeth (109) of the piston rod (110) as indicated in FIG. 5. The action of the axle (128) of the gear (113) positively engaging the set of teeth (109) of the piston rod (110) under the force provided by the flexible rack (108) of the internal housing (107) creates an audible and tactile feedback to the user to indicate that the dose has been set. Additionally, visual feedback regarding dose setting may optionally be indicated by a graphical status indicator, provided on the drive member (114), which can be viewed through an optional window aperture in the main housing part (103).

When the dose has been set, the user may then dispense this dose by depressing the dispensing face (119) of the activation part (116) of the drive member (114). By this action the drive member (114) and the rack (115) are moved axially in the distal direction relative to the main housing part (103). As the teeth of the gear (113) are engaged with the teeth of the rack (115) and the teeth of the flexible rack (108) of the internal housing (107) the gear (113) is rotated and moved in the distal direction. The axle (128) of the gear (113) is engaged with the set of teeth (109) of the piston rod (110), thereby causing the piston rod (110) to move longitudinally in the distal direction with respect to the internal housing (107).

The distal axial movement of the piston rod (110) causes the bearing surface (112) of the piston rod (110) to bear against the piston (105) of the cartridge (104) causing a dose of medicament to be dispensed through the attached needle (not shown).

The distal travel of the drive member (114) is limited by the guide slots (not shown) of the internal housing (107). Audible and tactile feedback to indicate that the dose has been dispensed is provided by the interaction of the pawl means (121) of the internal housing (107) with the set of teeth (109) of the piston rod (110). Additionally, visual feedback regarding dose dispensing may optionally be indicated by a graphical status indicator, provided on the drive member (114), which can be viewed through an optional window aperture in the main housing part (103).

Further doses may be delivered as required up to a predetermined maximum number of doses.

Example 3

Referring to FIGS. 6 to 7, there is shown a further alternative embodiment of the drug delivery device in accordance with the present invention.

The drug delivery device (201) comprises a cartridge retaining part (202), and a main (exterior) housing part (203). The proximal end of the cartridge retaining part (202) and the distal end of the main housing (203) are secured together by any suitable means known to the person skilled in the art. In the illustrated embodiment, the cartridge retaining part (202) is secured within the distal end of the main housing part (203).

A cartridge (204) from which a number of doses of a medicinal product may be dispensed is provided in the cartridge retaining part (202). A piston (205) is retained in the proximal end of the cartridge (204).

The distal end of the cartridge retaining part (202) in the illustrated embodiment, is provided with a distal threaded region (206) designed for the attachment of a suitable needle assembly to enable medicament to be dispensed from the cartridge (204).

In the illustrated embodiment, the main housing part (203) is provided with an internal housing (207). The internal housing (207) is secured against rotational and/or axial movement with respect to the main housing part (203). The internal housing (207) is provided with a fixing point (208) for attaching a pulley (240). Alternatively, the internal housing (207) may be formed integrally with the main housing part (203). Additionally, the internal housing (207) is provided with a guide slot (not shown) and pawl means (not shown).

A piston rod (210) extending through the main housing (203) has a first set of teeth (209) and a second set of teeth (211) extending longitudinally along surfaces of the piston rod (210). The second set of teeth (211) of the piston rod (210) extends through and is engaged with the pawl means (not shown) of the internal housing (207) to prevent movement of the piston rod (210) in the proximal direction during setting of the device. A bearing surface (212) located at the distal end of the piston rod (210) is disposed to abut the proximal face of the piston (205).

A pulley (240), comprising a belt (241) and a wheel (242) is located within a channel within the piston rod (210). An axle (228) of the wheel (242) is releasably engaged with the first set of teeth (209) of the piston rod (210). The first set of teeth (209) are designed to allow force transmission to the piston rod (210) in the distal direction during dispense and to allow relative movement between the pulley (240) and the piston rod (210) in the proximal direction during setting. The teeth of the wheel (242) are permanently engaged with the teeth of the belt (241) of pulley (240).

A drive member (214) extends about the piston rod (210). The drive member (214) comprises a fixing point (215) and an activation part (216). The fixing point (215) and the activation part (216) are secured to each other to prevent rotational and/or axial movement there between. Alternatively, the drive member (214) may be a unitary component consisting of an integrated fixing point (215) and activation part (216).

The belt (241) of the pulley (240) is attached to the drive member (214) at the fixing point (215).

The drive member (214) has a guide lug (not shown) which is located in the guide slot (not shown) of the internal housing (207). This defines the extent of permissible axial movement of the drive member (214) with respect to the housing part (203). In the illustrated embodiment the guide slot also prevents rotational movement of the drive member (214) relative to the main housing part (203).

The activation part (216) of the drive member (214) has a grip surface (218) and a dispensing face (219).

To increase intuitiveness of the operation of the device, the main housing part (203) may be provided with an optional window aperture through which optional graphical status indicators, provided on the drive member (214), can be viewed.

Operation of the drug delivery device in accordance with the present invention will now be described.

To set a dose a user grips the grip surfaces (218) of the drive member (214). The user then pulls the drive member (214) in a proximal direction away from the main housing part (203) thereby moving the fixing point (215) in a proximal direction.

The proximal movement of the drive member (214) causes the wheel (242) of the pulley (240) to rotate and move proximally by virtue of the attachment of the belt (241) of the pulley (240) to both the fixing point (215) of the drive member (214) and the fixing point (208) of the internal housing (207).

The piston rod (210) is prevented from moving proximally by the interaction of pawl means (not shown) of the internal housing (207) with the second set of teeth (211) of the piston rod (210). As the drive member (214) travels in the proximal direction relative to the piston rod (210), the axle (228) of the wheel (242) is displaced transversely by interaction with the first set of teeth (209) of the piston rod (210) thus deflecting the belt (241) of the pulley (240).

The proximal travel of the drive member (214) is limited by the guide slot (not shown) of the internal housing (207). At the end of the travel of the drive member (214), the axle (228) of the wheel (242) engages with the next sequential tooth of the first set of teeth (209) of the piston rod (210) as indicated in FIG. 7. The action of the axle (228) of the wheel (242) positively engaging the first set of teeth (209) of the piston rod (210) under the force provided by the belt (241) of the pulley (240) creates an audible and tactile feedback to the user to indicate that the dose has been set. Additionally, visual feedback regarding dose setting may optionally be indicated by a graphical status indicator, provided on the drive member (214), which can be viewed through an optional window aperture in the main housing part (203).

When the dose has been set, the user may then dispense this dose by depressing the dispensing face (219) of the activation part (216) of the drive member (214). By this action the drive member (214) and the fixing point (215) are moved axially in the distal direction relative to the main housing part (203). As the belt (241) of the pulley (240) is attached to the fixing point (215) of the drive member (214) and the belt (241) of the pulley (240) is also attached to the fixing point (208) of the internal housing (207) the wheel (242) of the pulley (240) is rotated and moved in the distal direction by the engagement of the teeth of the belt (241) with the teeth of the wheel (242). The axle (228) of the wheel (242) of the pulley (240) is engaged with the first set of teeth (209) of the piston rod (210), thereby causing the piston rod (210) to move axially in the distal direction with respect to the internal housing (207).

The distal axial movement of the piston rod (210) causes the bearing surface (212) of the piston rod (210) to bear against the piston (205) of the cartridge (204) causing a dose of medicament to be dispensed through the attached needle (not shown).

The distal travel of the drive member (214) is limited by the guide slot (not shown) of the internal housing (207). Audible and tactile feedback to indicate that the dose has been dispensed is provided by the interaction of the pawl means (not shown) of the internal housing (207) with the second set of teeth (211) of the piston rod (210). Additionally, visual feedback regarding dose dispensing may optionally be indicated by a graphical status indicator, provided on the drive member (214), which can be viewed through an optional window aperture in the main housing part (203).

Further doses may be delivered as required up to a predetermined maximum number of doses.

Example 4

Figure 8:
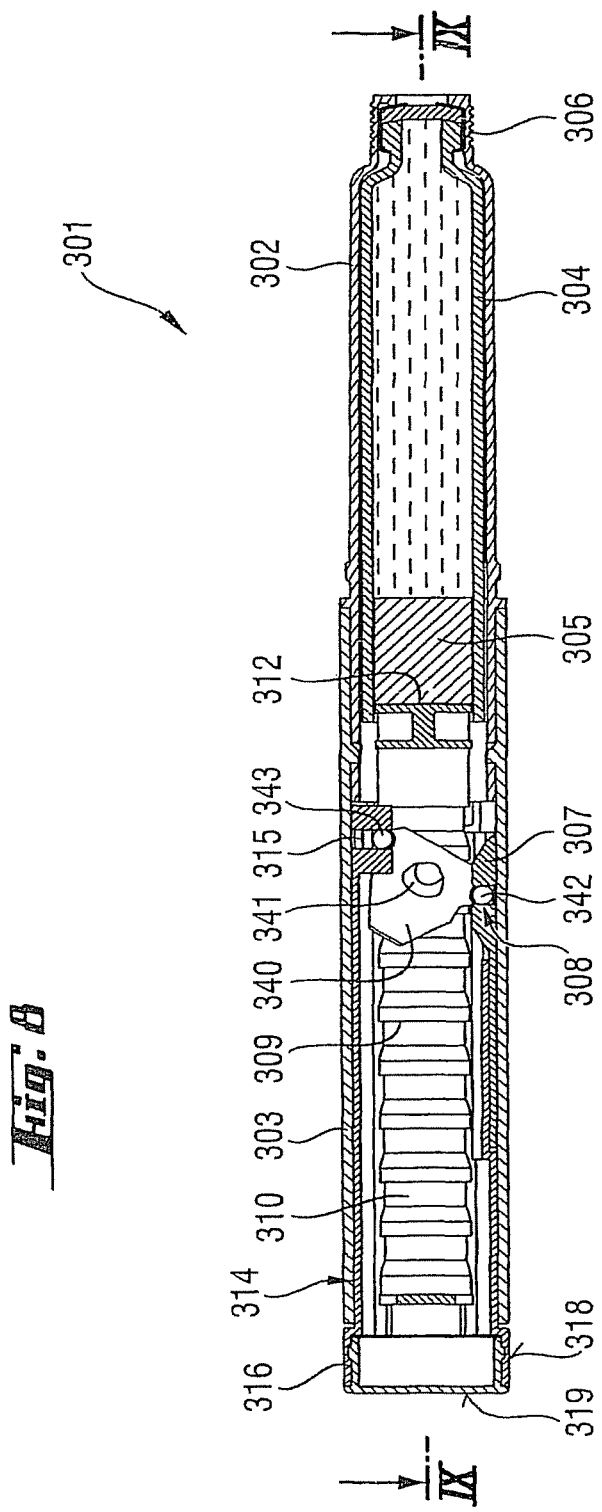
FIG. 8 shows a sectional view of a fourth embodiment of the drug delivery device in accordance with the present invention in a first, cartridge full, position.

Referring to FIGS. 8 to 10, there is shown a further alternative embodiment of the drug delivery device in accordance with the present invention.

The drug delivery device (301) comprises a cartridge retaining part (302), and a main (exterior) housing part (303). The proximal end of the cartridge retaining part (302) and the distal end of the main housing (303) are secured together by any suitable means known to the person skilled in the art. In the illustrated embodiment, the cartridge retaining part (302) is secured within the distal end of the main housing part (303).

A cartridge (304) from which a number of doses of a medicinal product may be dispensed is provided in the cartridge retaining part (302). A piston (305) is retained in the proximal end of the cartridge (304).

The distal end of the cartridge retaining part (302) in the illustrated embodiment, is provided with a distal threaded region (306) designed for the attachment of a suitable needle assembly (not shown) to enable medicament to be dispensed from the cartridge (304).

In the illustrated embodiment, the main housing part (303) is provided with an internal housing (307). The internal housing (307) is secured against rotational and/or axial movement with respect to the main housing part (303). The internal housing (307) is provided with a fulcrum point (308) for attaching a lever (340). Alternatively, the internal housing (307) may be formed integrally with the main housing part (303).

Additionally, the internal housing (307) is provided with a guide slots (not shown) and pawl means (345).

A piston rod (310) extending through the main housing (303) has a first set of indentations (309 and 309') and a second set of indentations (311 and 311') extending longitudinally along surfaces of the piston rod (310). The second net of indentations (311 and 311') of the piston rod (310) extends through and is engaged with the pawl means (345) of the internal housing (307) to prevent movement of the piston rod (310) in the proximal direction during setting of the device. A bearing surface (312) located at the distal end of the piston rod (310) is disposed to abut the proximal face of the piston (305).

A lever (340), comprising a plurality of lugs (341) and a first pivot (342) and a second pivot (343), is located within a channel within the piston rod (310). The lugs (341) of the lever (340) are releasably engaged with the first set of indentations (309 and 309') of the piston rod (310). The first set of indentations (309 and 309') are designed to allow force transmission to the piston rod (310) in the distal direction during dispense and to allow relative movement between the lever (340) and the piston rod (310) in the proximal direction during setting. The first pivot (342) of the lever (340) is attached to the fulcrum (308) of the internal housing (307) for pivotable movement there between.

A drive member (314) extends about the piston rod (310). The drive member (314) comprises a slot (315) and an activation part (316). The slot (315) and the activation part (316) are secured to each other to prevent rotational and/or axial movement there between. Alternatively, the drive member (314) may be a unitary component consisting of an integrated slot (315) and activation part (316).

The second pivot (343) of the lever (340) is located within the slot (315) of the drive member (314). The slot (315) of the drive member (314) is designed to allow transverse movement, but not longitudinal movement, of the second pivot (343) of the lever (340) relative to the drive member (314).

The drive member (314) has guide lugs (346) which are located in the guide slots (not shown) of the internal housing (307). This defines the extent of permissible axial movement of the drive member (314) with respect to the housing part (303). In the illustrated embodiment the guide slots also prevent rotational movement of the drive member (314) relative to the main housing part (303).

The activation part (316) of the drive member (314) has a grip surface (318) and a dispensing face (319).

To increase intuitiveness of the operation of the device, the main housing part (303) may be provided with an optional window aperture through which optional graphical status indicators, provided on the drive member (314), can be viewed.

Operation of the drug delivery device in accordance with the present invention will now be described.

To set a dose a user grips the grip surfaces (318) of the drive member (314). The user then pulls the drive member (314) in a proximal direction away from the main housing part (303) thereby moving the fixing point (315) in a proximal direction.

The proximal movement of the drive member (314) causes the lever (340) to rotate about the fulcrum (308) of the internal housing (307) in a proximal direction by virtue of the location of the second pivot (343) of the lever (340) within the slot (315) of the drive member (314).

The piston rod (310) is prevented from moving proximally by interaction of pawl means (345) of the internal housing (307) with the second set of indentations (311 and 311') of the piston rod (310). As the drive member (314) travels in the proximal direction relative to the piston rod (310), the lugs (341) of the lever (340) are displaced transversely by interaction with the first set of indentations (309 and 309') of the piston rod (310).

The proximal travel of the drive member (314) is limited by the guide slots (not shown) of the internal housing (307). At the end of the travel of the drive member (314), the lugs (341) of the lever (340) engage with the next sequential indentation of the first set of indentations (309 and 309') of the piston rod (310) as indicated in FIG. 10. The action of the lugs (341) of the lever (340) positively engaging the first set of indentations (309 and 309') of the piston rod (310) under a force provided by the transverse deflection of the lever (340) creates an audible and tactile feedback to the user to indicate that the dose has been set. Additionally, visual feedback regarding dose setting may optionally be indicated by a graphical status indicator, provided on the drive member (314), which can be viewed through an optional window aperture in the main housing part (303).

When the dose has been set, the user may then dispense this dose by depressing the dispensing face (319) of the activation part (316) of the drive member (314). By this action the drive member (314) and the slot (315) are moved axially in the distal direction relative to the main housing part (303). As the second pivot (343) of the lever (340) is located within the slot (315) of the drive member (314), the lever (340) is rotated about the fulcrum (308) of the internal housing (307) in the distal direction. The lugs (341) of the lever (340) are engaged with the first set of indentations (309 and 309') of the piston rod (310), thereby causing the piston rod (310) to move axially in the distal direction with respect to the internal housing (307).

The distal axial movement of the piston rod (310) causes the bearing surface (312) of the piston rod (310) to bear against the piston (305) of the cartridge (304) causing a dose of medicament to be dispensed through the attached needle (not shown).

The distal travel of the drive member (314) is limited by the guide slots (not shown) of the internal housing (307). Audible and tactile feedback to indicate that the dose has been dispensed is provided by the interaction of the pawl means (345) of the internal housing (307) with the second set of indentations (311 and 311') of the piston rod (310). Additionally, visual feedback regarding dose dispensing may optionally be indicated by a graphical status indicator, provided on the drive member (314), which can be viewed through an optional window aperture in the main housing part (303).

Further doses may be delivered as required up to a predetermined maximum number of doses.

Example 5

Referring to FIGS. 11 to 12, there is shown a further alternative embodiment of the drug delivery device in accordance with the present invention.

The drug delivery device (401) comprises a cartridge retaining part (402), and a main (exterior) housing part (403). The proximal end of the cartridge retaining part (402) and the distal end of the main housing (403) are secured together by any suitable means known to the person skilled in the art. In the illustrated embodiment, the cartridge retaining part (402) is secured within the distal end of the main housing part (403).

A cartridge (404) from which a number of doses of a medicinal product may be dispensed is provided in the cartridge retaining part (402). A piston (405) is retained in the proximal end of the cartridge (404).

A removable cap (422) is releasably retained over the distal end of the cartridge retaining part (402). The removable cap (422) is optionally provided with one or more window apertures through which the position of the piston (405) within the cartridge (404) can be viewed.

The distal end of the cartridge retaining part (402) in the illustrated embodiment, is provided with a distal threaded region (406) designed for the attachment of a suitable needle assembly (not shown) to enable medicament to be dispensed from the cartridge (404).

In the illustrated embodiment, the main housing part (403) is provided with an internal housing (407). The internal housing (407) is secured against rotational and/or axial movement with respect to the main housing part (403). The internal housing (407) is provided with a fulcrum (408). Alternatively, the internal housing (407) may be formed integrally with the main housing part (403). Additionally, the internal housing (407) is provided with a plurality of guide lugs (not shown) and pawl means (not shown). The pawl means may be an integrated part of the internal housing (407) or may be a separate component as illustrated.

A piston rod (410) extending through the main housing (403) has a first set of indentations (not shown) extending longitudinally along external surfaces of the piston rod (410). A second set of indentations (411) extend longitudinally along internal surfaces of the piston rod (410). The first set of indentations of the piston rod (410) extend through and are engaged with the pawl means of the internal housing (407) to prevent movement of the piston rod (410) in the proximal direction during setting of the device. A bearing surface (412) located at the distal end of the piston rod (410) is disposed to abut the proximal face of the piston (405). In the illustrated embodiment the longitudinal spacing of the first set of indentations and the second set of indentations (411) is essentially equal.

A lever assembly (413), consisting of a carrier (428) and a lever (427), free to rotate within the carrier (428), is located within a channel within the piston rod (410). The lever (427) is provided with a first pivot (442) and a second pivot (443). Pawl arms (429) located on the carrier (428) are releasably engaged with the second set of indentations (411) of the piston rod (410). The pawl arms (429) of the carrier (428) are designed to transmit force to the piston rod (410) in the distal direction during dispense and to allow relative movement between the lever assembly (413) and the piston rod (410) in the proximal direction during setting. The first pivot (442) of the lever (427) is attached to the fulcrum (408) of the internal housing (407) for pivotable movement there between.

A drive member (414) extends about the piston rod (410). The drive member (414) comprises a slotted part (415) and an activation part (416). The slotted part (415) and the activation part (416) are secured to each other to prevent rotational and/or axial movement there between. Alternatively, the drive member (414) may be a unitary component consisting of an integrated slotted part (415) and activation part (416).

The slotted part (415) is provided with a slot (417) that is essentially perpendicular to the main axis of the drive member (414). The second pivot (443) of the lever (427) is located within the slot (417) of the internal housing (407). The slot (415) of the drive member (414) is designed to allow transverse movement, but not longitudinal movement, of the second pivot (443) of the lever (427) relative to the drive member (414).

The drive member (414) has a plurality of guide slots (not shown) in which the guide lugs (not shown) of the internal housing (407) are located. These guide slots define the extent of permissible axial movement of the drive member (414) with respect to the housing part (403). In the illustrated embodiment the guide slots also prevent rotational movement of the drive member (414) relative to the main housing part (403).

The activation part (416) of the drive member (414) has a plurality of grip surfaces (418) and a dispensing face (419).

To increase intuitiveness of the operation of the device, the main housing part (403) may be provided with an optional window aperture through which optional graphical status indicators, provided on the drive member (414), can be viewed.

Operation of the drug delivery device in accordance with the present invention will now be described.

To set a dose a user grips the grip surfaces (418) of the drive member (414). The user then pulls the drive member (414) in a proximal direction away from the main housing part (403) thereby moving the slotted part (415) in a proximal direction.

The proximal movement of the drive member (414) causes the lever (427) to rotate about the fulcrum (408) of the internal housing (407) in a proximal direction by virtue of the location of the second pivot (443) of the lever (427) within the slot (417) of the drive member (414).

The piston rod (410) is prevented from moving proximally by interaction of pawl means (not shown) of the internal housing (407) with the first set of indentations (not shown) of the piston rod (410). As the drive member (414) travels in the proximal direction relative to the piston rod (410), the pawl arms (429) of the carrier (428) are displaced inwardly by interaction with the second set of indentations (411) of the piston rod (410).

The proximal travel of the drive member (414) is limited by the guide slots (not shown) of the slotted part (415). At the end of the travel of the drive member (414), the pawl arms (429) of the carrier (428) engage with the next sequential indentation of the second set of indentations (411) of the piston rod (410) as indicated in FIG. 12. The action of the pawl arms (429) of the carrier (428) positively engaging the second set of indentations (411) of the piston rod (410) creates an audible and tactile feedback to the user to indicate that the dose has been set. Additionally, visual feedback regarding dose setting may optionally be indicated by a graphical status indicator, provided on the drive member (414), which can be viewed through an optional window aperture in the main housing part (403).

When the dose has been set, the user may then dispense this dose by depressing the dispensing face (419) of the activation part (416) of the drive member (414). By this action the drive member (414) and the slotted part (415) are moved axially in the distal direction relative to the main housing part (403). As the second pivot (443) of the lever (427) is located within the slot (417) of the drive member (414), the lever (427) is rotated about the fulcrum (408) of the internal housing (407) in the distal direction. As the pawl arms (429) of the carrier (428) of the lever assembly (413) are engaged with the second set of indentations (411) of the piston rod (410), the piston rod (410) is caused to move longitudinally in the distal direction with respect to the internal housing (407).

The distal axial movement of the piston rod (410) causes the bearing surface (412) of the piston rod (410) to bear against the piston (405) of the cartridge (404) causing a dose of medicament to be dispensed through the attached needle.

The distal travel of the drive member (414) is limited by the guide slots (not shown) of the slotted part (415). Audible and tactile feedback to indicate that the dose has been dispensed is provided by the interaction of the pawl means (not shown) of the internal housing (407) with the first set of indentations (not shown) of the piston rod (410). Additionally, visual feedback regarding dose dispensing may optionally be indicated by a graphical status indicator, provided on the drive member (414), which can be viewed through an optional window aperture in the main housing part (403).

Further doses may be delivered as required up to a predetermined maximum number of doses.

The invention claimed is:

1. A drive mechanism for use with a delivery device, the drive mechanism comprising:
 a rack that is moveable in a proximal direction and in a distal direction;
 a piston rod coupled with said moveable rack, said piston rod comprising a first plurality of indentations along at least a portion of said piston rod; and
 a rotating component engaged with said movable rack such that it transfers movement between said movable rack and said piston rod, said rotating component releasably engaged with said first plurality of indentations of said piston rod, and a carrier releasable engaged with said piston rod, said carrier allowing relative movement between said rotating component and said piston rod.

2. The drive mechanism of claim 1 wherein when said drive mechanism is used to set a dose of a medicament contained within a drug delivery device, said rack is moved proximally with respect to said piston rod.

3. The drive mechanism of claim 2 wherein when said drive mechanism is used to set of dose of a medicament contained within a drug delivery device, said rotating component moves proximally with respect to said piston rod.

4. The drive mechanism of claim 3 further comprising a drive member operatively coupled to said movable rack
such that when said drive member is moved in the proximal direction with respect to said piston rod, said moveable rack is also moved in proximally with respect to said piston rod.

5. The drive mechanism of claim 1 wherein said piston rod further comprises a second plurality of indentations, said second plurality of indentations residing along an external surface of said piston rod.

6. The drive mechanism of claim 5 wherein said second plurality of indentations are configured to releasably engage a housing of a drug delivery device so as to prevent said piston rod from moving in a proximal direction.

7. The drive mechanism of claim 1 wherein said drive mechanism is configured to be coupled to a cartridge retaining part.

8. The drive mechanism of claim 7 wherein said drive mechanism is configured to be releasably coupled to the cartridge retaining part.

9. The drive mechanism of claim 1 wherein said drive mechanism can be used to administer one or more pre-set doses of a medicament contained within a drug delivery device.

10. The drive mechanism of claim 1 wherein said rotating component comprises a gear, said gear comprising said carrier and a gear wheel.

11. The drive mechanism of claim 1 wherein said carrier is operatively coupled to said piston rod.

* * * * *